United States Patent [19]

Kurz

[11] Patent Number: 5,104,401
[45] Date of Patent: Apr. 14, 1992

[54] AUDITORY OSSICLES PROSTHESIS

[76] Inventor: Heinz Kurz, Tübinger Strasse 3, D-7401 Dusslingen, Fed. Rep. of Germany

[21] Appl. No.: 465,455

[22] Filed: Jan. 16, 1990

[30] Foreign Application Priority Data

Jan. 21, 1989 [DE] Fed. Rep. of Germany ....... 3901796

[51] Int. Cl.⁵ .............................................. A61F 2/18
[52] U.S. Cl. .................................................... 623/10
[58] Field of Search ............................... 623/10, 11, 16

[56] References Cited

U.S. PATENT DOCUMENTS

| | | | |
|---|---|---|---|
| 3,710,399 | 1/1973 | Hurst | 623/10 |
| 3,909,852 | 10/1975 | Homsy | 623/10 |
| 4,601,723 | 7/1986 | McGrew | 623/10 |
| 4,624,672 | 11/1986 | Lenkauskas | 623/10 |
| 4,740,209 | 4/1988 | Gersdorff | 623/10 |
| 4,871,364 | 10/1989 | Bays et al. | 623/10 |

Primary Examiner—David J. Isabella
Attorney, Agent, or Firm—Michael J. Striker

[57] ABSTRACT

An auditory ossicles prosthesis for vibration transmitting comprises a surface for abutting aginst an ear drum, and a post extending from the surface and having an end provided with a thickening, the surface and the post being composed of a material selected from the group consisting of gold and titanium, the post being formed as a gold wire.

12 Claims, 1 Drawing Sheet

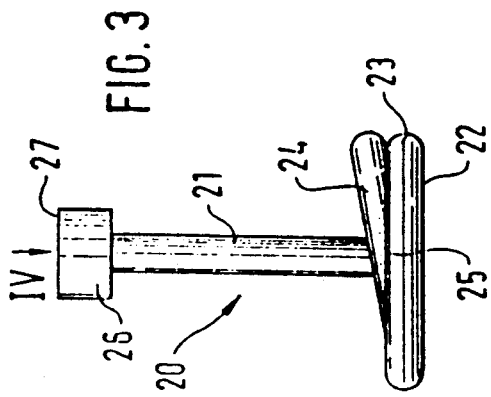
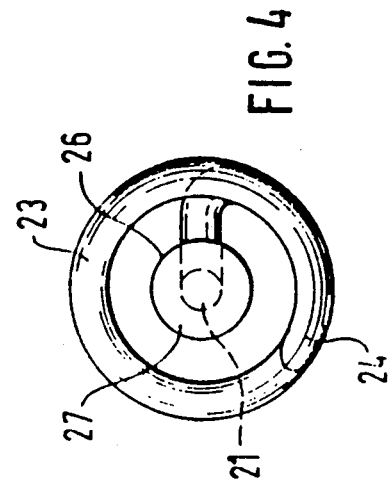
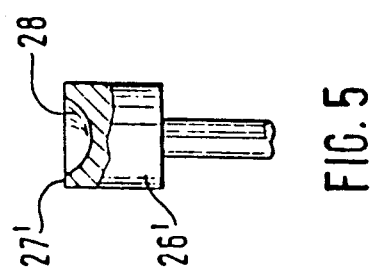
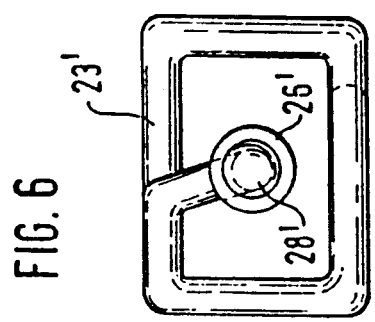
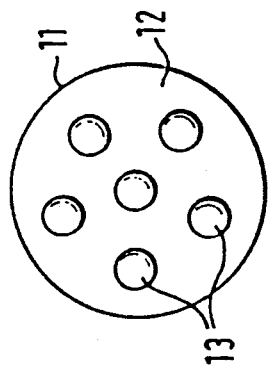
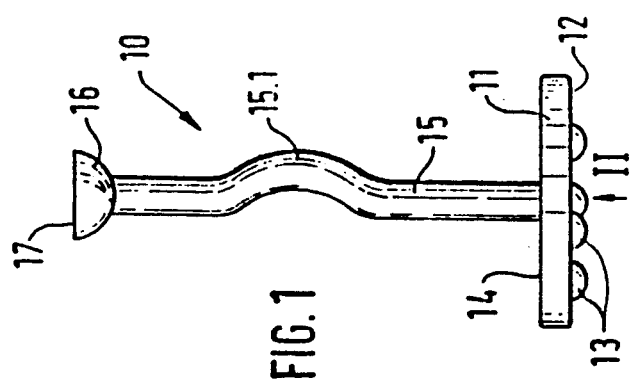

AUDITORY OSSICLES PROSTHESIS

BACKGROUND OF THE INVENTION

The present invention relates to an auditory ossicles prosthesis. More particularly, it relates to an auditory ossicles prosthesis which serves as a vibration transmitting element and has a surface for abutting against the ear drum and a post extending from the surface and provided with a thickening.

Auditory ossicles prostheses of the above mentioned general type are known. The known prostheses are composed of ceramics and widely used. They have however the disadvantage that they have relatively high volume and lead partially to skin irritation and inflammations in the region of their use. In other words, they are not compatible for the body of each patient.

SUMMARY OF THE INVENTION

Accordingly, it is an object of the present invention to provide an auditory ossicles prosthesis which avoids the disadvantages of the prior art.

More particularly, it is an object of the present invention to provide such auditory ossicles prosthesis which has a high compatibility with bodies of patients.

In keeping with these objects and with others which will become apparent hereinafter, one feature of the present invention resides, briefly stated, in an auditory ossicles prosthesis which is composed of a pure (fine) gold and at least its post is formed by a gold wire.

In accordance with another advantageous feature of the present invention, the post is provided with means for changing a distance between an abutment surface and a thickened end region of the post. This means can be formed as a curved region on the post. Also, the auditory ossicles prosthesis in accordance with the present invention can be composed partially or completely of titanium.

When the auditory ossicles prosthesis is formed in accordance with the present invention, it can be made very thin and composed of a material which is known for its high compatibility with bodies. By providing a length changing means for example a curved region on the post, the total length of the post can be adjusted during the operational insertion of the prosthesis to individual properties of a patient.

The abutment surface of the auditory ossicles prosthesis can be formed as a fine gold disc. Such a disc can be provided with knob-like projections to distribute the abutment pressure on the ear drum over several regions. On the other hand, it provides an efficient securing against a sliding of the prosthesis from the inner side of the ear drum. An increased adhesion of the abutment surface to mucus skin can be obtained by roughening of the abutment surface.

In accordance with a further preferable embodiment of the invention, the auditory ossicles prosthesis is formed as a one-piece element composed of a fine gold wire. The abutment surface can be formed by a spiral or at least one coil formed from the wire and having a curved or cornered limiting line. This embodiment is especially preferably for simple manufacture. Also, here a linear abutment of the prosthesis against the ear drum is achieved. At the same time, this abutment is performed over a great linear length. Thereby only small ear drum regions are covered by the prosthesis and an inflammation danger is eliminated.

Length differences of the post of the prosthesis can be compensated without additional curves of the fine gold wire in the post region from the wire spiral or wire coil, or provided in the spiral or the coil. In each case, the fine gold auditory ossicles prosthesis is formed with burr-free edges. In the prosthesis with spirals or coils, the respective ends can be welded to the spiral or the coil in a burr-free manner, for example by laser welding.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side view of an auditory ossicles prosthesis in accordance with an embodiment of the invention;

FIG. 2 is a plan view of an abutment surface of the auditory ossicles prosthesis seen in direction of the arrow II in FIG. 1;

FIG. 3 is a side view of a second embodiment of an auditory ossicles prosthesis of the present invention;

FIG. 4 is a plan view of the auditory ossicles prosthesis as seen in direction of the arrow IV in FIG. 3;

FIG. 5 is a partial side view, partially in section, of a different prosthesis of FIGS. 3 and 4; and FIG. 6 is a plan view substantially corresponding to the view of FIG. 4 and showing a corner-shaped coil of the prosthesis.

DESCRIPTION OF THE PREFERRED EMBODIMENTS

An auditory ossicles prosthesis shown in FIGS. 1 and 2 is identified as a whole with reference numeral 10. It has a disc 11 composed of fine gold and forming an abutment surface 12 with its one side. The ear drum of a patient abuts against the abutment surface 12. The abutment surface 12 is provided with a plurality of knob-like projections 13 which are uniformly distributed over this surface. A post 15 is arranged centrally and particularly in the center of a rear side 14 of the disc 11. The post 15 is formed as a wire composed of a fine gold.

A thickening 16 is formed on a free end of the post 15 and has a shape of a spherical calotte 16. The spherical calotte 16 forms a flat circular contact surface 17. The post 15 in its center has a curved region 15.1 which forms a length reserve. It permits an extension of the side distance from the fine gold disc 11 and to the fine gold spherical calotte.

FIGS. 3 and 4 show a auditory ossicles prosthesis 20 which is formed as a one-piece integral member composed of a fine gold wire. The basic form of the prosthesis substantially corresponds to the basic form of the prosthesis shown in FIGS. 1 and 2. However, here a post 21 of the prosthesis extends rectilinearly over its whole length. An abutment surface 22 of the auditory ossicles prosthesis 20 is formed by winding of a coil 23 which is bent from the fine gold wire. An end region 24 of the fine gold wire is firmly welded with the rear side of the winding of the coil 23 which forms the abutment surface 22. The welding can be performed by a laser welding process. A welding seam 25 can be seen in FIG. 3. The free end of the poles 21 is formed by thickening of the fine gold wire. The thickening forms a roller body 26 which forms a flat contact surface 27 similar to the embodiment of FIGS. 1 and 2.

Instead of a wire coil 23, also a wire spiral can be formed. The abutment surface 22 formed by it can be roughened for improving its adhesion. The wire coil 23 must not necessarily have a circular form. It can be limited by an oval or a rectangular abutment surface, which latter is shown in FIG. 6. A length reserve for the post 21 is formed here by the wire coil 23 or the wire spiral. Therefore also in this embodiment of auditory ossicles prosthesis, during the operation the distance between the contact surface 22 and the abutment surface 27 can be individually adjusted. In FIG. 6 similar parts are identified with the same reference numerals and with addition of primes.

FIG. 5 shows an end 26' of the roller body of an auditory ossicles partial prosthesis. Here a depression 28 is formed in a contact surface 27'. A riser can be introduced into the depression.

It will be understood that each of the elements described above, or two or more together, may also find a useful application in other types of constructions differing from the types described above.

While the invention has been illustrated and described as embodied in an auditory ossicles prosthesis formed as a vibration transmitting element, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An auditory ossicles prosthesis for vibration transmitting, comprising abutment means forming a surface for abutting against an ear drum, a post extending from said surface and having an end, a thickening provided on said end of said post, said prosthesis as a whole being formed as a one-piece element, said surface, said post and said thickening being composed of a material selected from the group consisting of gold and titanium, said post being formed as a wore which includes at least one curved part and is malleable whereby the distance between said abutment surface and said end of said post can be changed by changing the shape of said curved part.

2. An auditory ossicles prosthesis as defined in claim 1, wherein said thickening provided on said end of said post is formed as a roller.

3. An auditory ossicles prosthesis as defined in claim 1, wherein said thickening provided on said end of said post has a flat contact surface.

4. An auditory ossicles prosthesis as defined in claim 1, wherein said thickening of said end of said post has a contact side provided with a depression.

5. An auditory ossicles prosthesis as defined in claim 1, wherein said prosthesis as a whole is composed of a wire, said wire having a portion forming said abutment surface.

6. An auditory ossicles prosthesis as defined claim 5, wherein said curved part of said means for changing includes a coil formed by said portion of said wire.

7. An auditory ossicles prosthesis as defined in claim 5, wherein said portion of said wire is rectangular.

8. An auditory ossicles prosthesis as defined in claim 5, wherein said portion of said wire is round.

9. An auditory ossicles prosthesis as defined in claim 5, wherein said post has an opposite end which is connected to said coil of said wire.

10. An auditory ossicles prosthesis as defined in claim 1, wherein said abutment surface is round.

11. An auditory ossicles prosthesis as defined in claim 1, wherein said prosthesis at least partially is composed of titanium.

12. An auditory ossicles prosthesis for vibration transmitting, comprising a disc shaped abutment means forming a surface, said surface being provided with a plurality of knob-shaped projections for abutting an ear drum; and a wire post extending outwardly from said surface terminating at a thickened opposite end, said abutment means and said wire post being of a material selected from the group consisting of gold and titanium.

* * * * *